(12) United States Patent
Wei

(10) Patent No.: US 9,539,296 B2
(45) Date of Patent: Jan. 10, 2017

(54) EYE-REFRESHING AGENT TO ELIMINATE AND ALLEVIATE EYE FATIGUE AND DISCOMFORT

(71) Applicant: Jianxue Wei, Xi'an (CN)

(72) Inventor: Jianxue Wei, Xi'an (CN)

(*) Notice: Subject to any disclaimer, the term of this patent is extended or adjusted under 35 U.S.C. 154(b) by 0 days.

(21) Appl. No.: 14/783,203

(22) PCT Filed: Feb. 21, 2014

(86) PCT No.: PCT/CN2014/072369
§ 371 (c)(1),
(2) Date: Oct. 8, 2015

(87) PCT Pub. No.: WO2014/166316
PCT Pub. Date: Oct. 16, 2014

(65) Prior Publication Data
US 2016/0067297 A1    Mar. 10, 2016

(30) Foreign Application Priority Data

Apr. 8, 2013   (CN) .......................... 2013 1 0120236

(51) Int. Cl.
| | |
|---|---|
| *A01N 65/00* | (2009.01) |
| *A61K 36/61* | (2006.01) |
| *A61K 31/045* | (2006.01) |
| *A61K 36/48* | (2006.01) |
| *A61K 36/534* | (2006.01) |
| *A61Q 19/00* | (2006.01) |
| *A61Q 19/08* | (2006.01) |
| *A61K 8/97* | (2006.01) |
| *A61K 36/54* | (2006.01) |

(52) U.S. Cl.
CPC ............... *A61K 36/61* (2013.01); *A61K 8/97* (2013.01); *A61K 31/045* (2013.01); *A61K 36/48* (2013.01); *A61K 36/534* (2013.01); *A61K 36/54* (2013.01); *A61Q 19/005* (2013.01); *A61Q 19/08* (2013.01); *A61K 2236/00* (2013.01); *A61K 2236/331* (2013.01); *A61K 2236/53* (2013.01)

(58) Field of Classification Search
CPC ...................................................... A61K 36/00
USPC .......................................................... 424/725
See application file for complete search history.

(56) References Cited

U.S. PATENT DOCUMENTS

2010/0137252 A1    6/2010   Matsumura et al.

FOREIGN PATENT DOCUMENTS

| CN | 1320439 A | 11/2001 |
|---|---|---|
| CN | 2638833 Y | 9/2004 |
| CN | 1604794 A | 4/2005 |
| CN | 101015540 A | 8/2007 |
| CN | 101439091 A | 5/2009 |
| CN | 102349865 A | 2/2012 |
| EP | 1457212 A1 | 9/2004 |

OTHER PUBLICATIONS

European Search Report for European Application No. 14782559.0 dated Mar. 15, 2016. (7 pages).
Office Action for Chinese Application No. 201310120236.4 dated Feb. 5, 2016. (5 pages).
International Search Report issued in corresponding application No. PCT/CN2014/072369, mailed Jun. 3, 2014.
International Preliminary Examination Report issued in corresponding application No. PCT/CN2014/072369 on Oct. 13, 2015, along with an English translation of the Written Opinion of the International Searching Authority dated Jun. 3, 2014.

*Primary Examiner* — Michael Meller
(74) *Attorney, Agent, or Firm* — Carter, DeLuca, Farrell & Schmidt, LLP

(57) ABSTRACT

An eye-refreshing agent, the raw materials of which include mung bean germs, eucalyptus leaves, mint leaves, clove leaves, camphor leaves and borneol. The plant cells thereof are respectively subjected to crushing, low-temperature freezing and centrifugation and sound membrane separation to prepare a water-soluble preparation. The preparation can prevent and alleviate visual fatigue and accelerate metabolism of the eye skin cells, and also has the effect of alleviating and improving eye bags and eye pseudo-wrinkles caused by eye fatigue.

2 Claims, No Drawings

EYE-REFRESHING AGENT TO ELIMINATE AND ALLEVIATE EYE FATIGUE AND DISCOMFORT

TECHNICAL FIELD

The present invention belongs to the field of pharmaceutical preparation technology, and particularly relates to an eye-refreshing agent for eliminating and alleviating eye fatigue and discomfort which is prepared by using natural fresh medicinal plants as raw materials, and also relates to a method for preparing the same.

BACKGROUND ART

Over the past decade, with the fast-paced development of social life and the widespread use of networks, the time that people use eyes has increased a lot, especially persons who surf the Internet, IT industry practitioners, drivers of coach buses and long-distance trucks as well as current students and the like. Because the time that they attentively use eyes has prolonged, visual fatigue has become a major factor affecting eye health. Currently, the number of netizen in the world has increased progressively in many folds every year. The number of netizen only in China has already been more than 300 million. A netizen surfs the Internet for about eight hours on average everyday. In addition to the netizen, now administrative staffs in China have already entered an era of working with a computer called automation office. The daily period of time of working online is more than four hours on average. Eye fatigue frequently affects work efficiency and leads to an eye disease. Moreover, the time that a driver of long-distance transport drives continuously more than four hours on average, and sometimes even more than 6 hours, thus serious accidents caused by eye visual fatigue occur frequently. For elderly, the phenomena such as physiological dry, astringent, ghosting, and blurred vision and so on of eyes caused by a prolonged use of eyes and other functional organic causes, and the phenomena such as physiological dry, astringent and the like appearing in the aging eye also severely affect their body health and life quality.

The visual fatigue of eyes mainly results from the eye fatigue and the eye skin cell fatigue, direct results of both of which cause the visual fatigue of eyes. The visual fatigue of the eyes most directly takes the form of dry eyes, swelling, ghosting, blurred vision and dark circles. In severe case, the phenomena such as increased eye bags, decreased vision, increased eye wrinkles and so on would occur. In the past, these problems were mainly solved by using eye drops to increase moisture of eyes, which however cannot address fundamentally the problem of eye skin cell fatigue and the phenomena such as physiological dryness and astringent of eyes that many elderly suffer from for long-term at the same time.

Currently, drugs for treating dry eyes are mainly eye drops and moisturizing-eye liquid and the like at home and abroad. The eye drops are mainly an antibiotics drug. Although having anti-inflammatory and antibacterial effects, the eye drops cannot play a role in alleviating visual fatigue of eyes. However, a product like the moisturizing-eye liquid is mainly a drug such as humectant, which has a moisturizing effect on eyes, but cannot alleviate visual fatigue.

Although ophthalmic drugs currently available on the market have anti-inflammatory, antibacterial, and moisturizing effects, there is no such a drug that can take into account the problems of alleviating the visual fatigue and eye cloudy caused by the prolonged use of eyes.

DETAILED DESCRIPTION

An object of the present invention is to solve the problems in the prior art, and provide an eye-refreshing agent for eliminating and alleviating eye fatigue and discomfort, with the eye-refreshing agent made of natural plants. The eye-refreshing agent can alleviate and eliminate symptoms such as dry eyes, swelling, ghosting, blurred vision, and dark circles and so on caused by the visual fatigue, and phenomena such as elderly dry eyes, astringent, and itching. It also has the capability to accelerate the metabolism of eye skin cells, thereby achieving effect of improving the refreshing degree of vision, and preventing and eliminating the visual fatigue, and as well as has the effects of alleviating and improving the eye bags and eye pseudo-wrinkles and so on caused by the visual fatigue.

The technical solution of the present invention for solving the problems in the prior art is obtained by the designer based on the analysis data of the effect of the selected natural plant ingredients on eye skin cells of human, as well as based on practical experience and knowledge about the effect for alleviating and improving eye visual fatigue which is generated by the clinical administration of the drug to the eye. It is a pure natural eye-refreshing agent dedicated for alleviating and improving the visual fatigue phenomena of human's eye skin caused by the prolonged use of the eyes, which is prepared by using a modern biotechnology. The eye-refreshing agent is an eye skin external-use care agent, which is prepared from mung bean germ, eucalyptus leaves, clove leaves, mint leaves, camphor, and borneol as raw materials, and in the drug form of spraying agent, ointment, eye patch or aqueous agent, and the eye-refreshing agent has effective pharmaceutical components, which include the raw materials of the following components parts by weight:

sound-membrane separation extract (extracting solution) of mung bean germ, 10 to 80, sound-membrane separation extract of eucalyptus leaves, 10 to 80, sound-membrane separation extract of mint leaves, 5 to 50, sound-membrane separation extract of clove leaves, 5 to 50, sound-membrane separation extract of camphor leaves, 1 to 10, borneol 0.1 to 1.

The method for preparing the eye refreshing agent comprises the following steps:

1. preparing sound-membrane separation extract of mung bean germ, which includes: cutting up fresh mung bean germs coarsely and then mixing them with water of 0.3 to 0.5 times by weight; placing mixed solution into a ultrasonic cell crusher and crushing into cell slurry; performing a centrifugation treatment on the cell slurry through a centrifuge; taking out supernatant and then separating it through a sound membrane separator, thereby obtaining sound-membrane separation extract of mung bean germs, having a molecular weight of less than 6000 D;

2. preparing sound-membrane separation extract of eucalyptus leaves, which includes: mechanically breaking fresh eucalyptus leaves and then adding water of 0.5 to 0.6 times by weigh and mixing; placing mixed solution into an ultrasonic cell crusher and crushing into cell slurry; performing a centrifugation treatment on the cell slurry through a centrifuge; taking out supernatant and then separating it through a sound membrane separator, thereby obtaining sound-membrane separation extract of eucalyptus leaves, having a molecular weight of less than 6000 D;

3. preparing sound-membrane separation extract of mint leaves, which includes: breaking mechanically fresh mint leaves, and then mixing them with water of 0.5 to 0.6 times by weight; placing mixed solution into an ultrasonic cell crusher, and crushing into cell slurry; performing a centrifugation treatment on the cell slurry through a centrifuge; taking out supernatant and separating it through a sound membrane separator, so as to obtain sound-membrane separation extract of mint leaves, having a molecular weight of less than 6000 D;

4. preparing sound-membrane separation extract of clove leaves, which includes: breaking mechanically fresh clove leaves, and then mixing with water of 0.5 to 0.6 times by weight; placing mixed solution into an ultrasonic cell crusher, and then crushing into cell slurry; performing a centrifugation treatment on the cell slurry through a centrifuge; taking out supernatant and separating it through a sound membrane separator, so as to obtain sound-membrane separation extract of clove leaves, having a molecular weight of less than 6000 D;

5. preparing sound-membrane separation extract of camphor leaves, which includes: breaking mechanically fresh camphor leaves, and then mixing with water of 0.5 to 0.6 times by weight; placing mixed solution into an ultrasonic cell crusher and crushing into cell slurry; performing a centrifugation treatment on the cell slurry through a centrifuge; taking out supernatant and separating it through a sound membrane separator, so as to obtain sound-membrane separation extract of camphor leaves, having a molecular weight of less than 6000 D;

6. the above sound-membrane separation extracts are mixed and formulated, and then a frozen centrifugation is performed at a centrifugal rotation speed of 3000 rpm~4000 rpm for 10 to 20 minutes at a temperature ranging from 0 to 4° C., to remove sediments, and centrifugal liquid was separated again by a sound membrane separator, so as to obtain mixed sound-membrane separation extract, having a molecular weight of less than 6000 D;

7. the mixed sound-membrane separation extract obtained after the mixing and separation was mixed with borneol, and then prepared it into spraying agent, ointment, eye patch or aqueous agent according to the preparation process for the spraying agent, ointment, eye patch or aqueous agent.

In each of effective pharmaceutical ingredients of the eye refreshing agent of the present invention: green bean germ has the effects of cooling, detoxicating, and hydrating cells, and can enhance ability of the eye skin cell hydration and metabolism; eucalyptus leaves have the effect of cooling, refreshing and hydrating cell, and can also enhance ability of the eye skin cell hydration and metabolism; both mint leaves and clove leaves have the effect of cooling and refreshing, and can accelerate ability of eye skin cell metabolism; and camphor and borneol have the effects of refreshing and cooling, respectively.

The eye refreshing agent of the present invention is an eye skin care product which is prepared by selecting and using natural plant materials according to the technical requirements for the preparation of biological products, containing a plurality of effective ingredients such as plant polysaccharide, peptide, cell hydration factor, menthol, camphor, syringic alcohol, borneol and the like. The above effective ingredients have a low molecular weight, easy to be absorbed by eye skin, and have the effects of alleviating and eliminating eye visual fatigue, and at the same time also have the effects of improving dry eyes, swelling, blurred vision, dark circles, ghosting, eye bags caused by prolonged use of the eyes. They also have some improvement and prevention formation effects on the increased eye wrinkles and the formation of eye bags appearing in the elderly. Moreover, they also have significant improvement, alleviation and elimination effects on the elderly dry eyes, astringent, and itchy phenomena. In addition, the substances selected and used for the eye refreshing agents are natural plant materials, and do not contain chemical synthetic drugs and allergic substances, non-toxic and harmless to humans, and also have no any side effects such as allergenic stimulation to eye skin, integrating efficacy and safety as a whole, and thus they have a good application and promotion value.

To show the alleviation and elimination effects of the eye-refreshing agent of the present invention on the eye skin fatigue and visual fatigue, the present invention demonstrated, through the study on the preparation over several years and the repeated applications and trial practices (including the selection of the test of the eye visual fatigue phenomena such as dry eyes, swelling, ghosting, blurred vision, and dark circles symptoms), that the eye-refreshing agent has broad spectrum effects of improvement, alleviation and elimination of eye fatigue, so as to achieve the effects of refreshing eye vision, concentrating the visual attention and increasing eye moist feeling, thereby facilitating the enhancements of eye cell metabolism capacity and capillary circulation. In the preparation process, the effectiveness of the eye refreshing agent of the present invention depends on the eye fatigue alleviation situation, the alleviation of dry eyes, swelling, ghosting, blurred vision, and level of dark circles caused by the prolonged use of eyes as a standard, and the conspicuity depends on the elimination of eye visual fatigue and symptoms as a standard. Nearly 500 people were visited for the use situation of the eye skin care agent which is in spraying form. The interviewee uses the spray once per day, the dose of each time is about 0.5 ml, and its statistic results are as follows:

Statistic data are for 472 people, wherein the effectiveness is 100%, and the conspicuity is 97%.

EXAMPLES

Example 1

The production of soluble solution of eye refreshing agent has extraction steps and preparation steps as follows.

1. Preparing sound-membrane separation extract of mung bean germs, wherein the fresh green bean germs were coarsely cut and then mixed with water of 0.4 times by weight. Then the mixed solution was placed into an ultrasonic cell crusher to be crushed into cell slurry. A centrifugation treatment was performed on the cell slurry through a centrifuge (the centrifugal rotational speed of 3500 rpm, for 15 minutes), and then the supernatant was taken out, and separated through a sound membrane separator (same as below) designed by the present inventor, patent No. ZL 03262745.6, so as to obtain a cell stock solution (sound-membrane separation extract of mung bean germs) having a molecular weight of less than 6000 D, which was a pale yellow or colorless liquid, containing plant polysaccharides component.

2. Preparing sound-membrane separation extract of eucalyptus leaves, wherein fresh eucalyptus leaves were mechanically broken and then mixed with water of 0.5 times by weight. The mixed solution was placed into the ultrasonic cell crusher to be crushed into cell slurry. A centrifugation treatment was performed on the cell slurry through a centrifuge (the centrifugal rotational speed of 3500 rpm, for 15 minutes). Then, the supernatant was taken out and then be separated through a sound membrane separator, so as to obtain a cell stock solution (sound-membrane separation extract of eucalyptus leaves) having a molecular weight of less than 6000 D, which was a light green or colorless liquid, containing plant polysaccharides component.

3. preparing sound-membrane separation extract of mint leaves, wherein fresh mint leaves were mechanically broken, and then water of 0.5 times by weight was added and mixed. The mixed solution was placed into an ultrasonic cell crusher to be crushed into cell slurry. A centrifugation treatment was performed on the cell slurry through a centrifuge (the centrifugal rotational speed of 3500 rpm, for 15 minutes). The supernatant was taken out and then separated through a sound membrane separator, so as to obtain a cell stock solution of mint leaves (sound-membrane separation extract of mint leaves) having a molecular weight of less than 6000 D, which was a light yellow-green or colorless liquid, containing plant menthol component.

4. Preparing sound-membrane separation extract of clove leaves, wherein fresh clove leaves were mechanically broken, and then water of 0.5 times by weight was added and mixed. The mixed solution was placed into an ultrasonic cell crusher to be crushed into cell slurry. A centrifugation treatment was performed on the cell slurry through a centrifuge (the centrifugal rotational speed of 3500 rpm, for 15 minutes). The supernatant was taken out and then separated through a sound membrane separator, so as to obtain a cell stock solution of clove leaves (sound-membrane separation extract of clove leaves) having molecular weight of less than 6000 D, which as a light yellow-green or colorless liquid, containing plant syringic alcohol component.

5. preparing sound-membrane separation extract of camphor leaves, wherein fresh camphor leaves were mechanically broken, and then water of 0.5 times by weight was added and mixed. The mixed solution was placed into an ultrasonic cell crusher to be crushed it into cell slurry. A centrifugation treatment was performed on the cell slurry through a centrifuge (the centrifugal rotational speed of 3500 rpm, for 15 minutes). The supernatant was taken out and then separated through a sound membrane separator, so as to obtain a cell stock solution of camphor leaves (sound-membrane separation extract of camphor leaves) having a molecular weight of less than 6000 D, which is a light yellow-green or colorless liquid, containing plant camphors component.

6. Each of the above cell stock solutions and borneol were taken and formulated according to the following amounts by weight:
sound-membrane separation extract of mung bean germ 5000 g,
sound-membrane separation extract of eucalyptus leaves 5000 g,
sound-membrane separation extract of mint leaves 1000 g,
sound-membrane separation extract of clove leaves 1000 g,
sound-membrane separation extract of camphor leaves 500 g,
borneol 50 g.

7. The above sound-membrane separation extracts were mixed and formulated, and a high-speed centrifugation (the centrifugation rotational speed of 3500 rpm, for 15 minutes) was performed at a low temperature (0~4° C.). The residue was discarded, and the supernatant was remained. The supernatant was separated through a sound membrane separation technology to obtain a separation liquid having the molecular weight of less than 6000 D.

8. A cell stock solution obtained after the mixing and separation was mixed with borneol, to be prepared into a spraying agent according to a conventional preparation process of spraying agent, and was dispensed and packaged, so as to obtain a finished product.

Example 2

The soluble solution of eye refreshing agent was prepared as follows.

First, the sound-membrane separation extract of mung bean germs, the sound-membrane separation extract of eucalyptus leaves, the sound-membrane separation extract of mint leaves, the sound-membrane separation extract of clove leaves, and the sound-membrane separation extract of camphor leaves were parepared as Exmaple 1.

Then, the above sound-membrane separation extracts and borneol were weighted by parts by weight:
sound-membrane separation extract of mung bean germs 10,
sound-membrane separation extract of eucalyptus leaves 10,
sound-membrane separation extract of mint leaves 5,
sound-membrane separation extract of clove leaves 5,
sound-membrane separation extract of camphor leaves 1,
borneol 0.1.

The above sound-membrane separation extracts were mixed and formulated, and a high-speed centrifugation (the centrifugation rotational speed of 3500 rpm, for 15 minutes) was performed at a low temperature of 0° C. The residue was discarded, and the supernatant was remained. The supernatant was separated through a sound membrane separation technology to obtain a separation liquid having the molecular weight of less than 6000 D.

A cell stock solution obtained after the mixing and separation was mixed with borneol, to be prepared into a spraying agent according to a conventional preparation process of spraying agent, and was dispensed and packaged, so as to obtain a finished product.

Example 3

The soluble solution of eye refreshing agent was prepared as follows.

First, the sound-membrane separation extract of mung bean germs, the sound-membrane separation extract of eucalyptus leaves, the sound-membrane separation extract of mint leaves, the sound-membrane separation extract of clove leaves, and the sound-membrane separation extract of camphor leaves were parepared as Exmaple 1.

Then, the above sound-membrane separation extracts and borneol were weighted by parts by weight:
sound-membrane separation extract of mung bean germs 30,
sound-membrane separation extract of eucalyptus leaves 30,
sound-membrane separation extract of mint leaves 20,
sound-membrane separation extract of clove leaves 20,
sound-membrane separation extract of camphor leaves 4,
borneol 0.5.

The above sound-membrane separation extracts were mixed and formulated, and a high-speed centrifugation (the centrifugation rotational speed of 3500 rpm, for 15 minutes) was performed at a low temperature of 2° C. The residue was discarded, and the supernatant was remained. The supernatant was separated through a sound membrane separation technology to obtain a separation liquid having the molecular weight of less than 6000 D.

A cell stock solution obtained after the mixing and separation was mixed with borneol, to be prepared into a spraying agent according to a conventional preparation process of spraying agent, and was dispensed and packaged, so as to obtain a finished product.

Example 4

The soluble solution of eye refreshing agent was prepared as follows.

First, the sound-membrane separation extract of mung bean germs, the sound-membrane separation extract of eucalyptus leaves, the sound-membrane separation extract of mint leaves, the sound-membrane separation extract of clove leaves, and the sound-membrane separation extract of camphor leaves were parepared as Exmaple 1.

Then, the above sound-membrane separation extracts and borneol were weighted by parts by weight:
sound-membrane separation extract of mung bean germs 50,
sound-membrane separation extract of eucalyptus leaves 50,
sound-membrane separation extract of mint leaves 30,
sound-membrane separation extract of clove leaves 30,
sound-membrane separation extract of camphor leaves 6,
borneol 0.6.

The above sound-membrane separation extracts were mixed and formulated, and a high-speed centrifugation (the centrifugation rotational speed of 3500 rpm, for 15 minutes) was performed at a low temperature of 1° C. The residue was discarded, and the supernatant was remained. The supernatant was separated through a sound membrane separation technology to obtain a separation liquid having the molecular weight of less than 6000 D.

A cell stock solution obtained after the mixing and separation was mixed with borneol, to be prepared into a spraying agent according to a conventional preparation process of spraying agent, and was dispensed and packaged, so as to obtain a finished product.

Example 5

The soluble solution of eye refreshing agent was prepared as follows.

First, the sound-membrane separation extract of mung bean germs, the sound-membrane separation extract of eucalyptus leaves, the sound-membrane separation extract of mint leaves, the sound-membrane separation extract of clove leaves, and the sound-membrane separation extract of camphor leaves were parepared as Exmaple 1.

Then, the above sound-membrane separation extracts and borneol were weighted by parts by weight:
sound-membrane separation extract of mung bean germs 60,
sound-membrane separation extract of eucalyptus leaves 60,
sound-membrane separation extract of mint leaves 40,
sound-membrane separation extract of clove leaves 40,
sound-membrane separation extract of camphor leaves 8,
borneol 0.8.

The above sound-membrane separation extracts were mixed and formulated, and a high-speed centrifugation (the centrifugation rotational speed of 3500 rpm, for 15 minutes) was performed at a low temperature of 3° C. The residue was discarded, and the supernatant was remained. The supernatant was separated through a sound membrane separation technology to obtain a separation liquid having the molecular weight of less than 6000 D.

A cell stock solution obtained after the mixing and separation was mixed with borneol, to be prepared into a spraying agent according to a conventional preparation process of spraying agent, and was dispensed and packaged, so as to obtain a finished product.

Example 6

The soluble solution of eye refreshing agent was prepared as follows.

First, the sound-membrane separation extract of mung bean germs, the sound-membrane separation extract of eucalyptus leaves, the sound-membrane separation extract of mint leaves, the sound-membrane separation extract of clove leaves, and the sound-membrane separation extract of camphor leaves were parepared as Exmaple 1.

Then, the above sound-membrane separation extracts and borneol were weighted by parts by weight:
sound-membrane separation extract of mung bean germs 80,
sound-membrane separation extract of eucalyptus leaves 80,
sound-membrane separation extract of mint leaves 50,
sound-membrane separation extract of clove leaves 50,
sound-membrane separation extract of camphor leaves 10,
borneol 1.

The above sound-membrane separation extracts were mixed and formulated, and a high-speed centrifugation (the centrifugation rotational speed of 3500 rpm, for 15 minutes) was performed at a low temperature of 4° C. The residue was discarded, and the supernatant was remained. The supernatant was separated through a sound membrane separation technology to obtain a separation liquid having the molecular weight of less than 6000 D.

A cell stock solution obtained after the mixing and separation was mixed with borneol, to be prepared into a spraying agent according to a conventional preparation process of spraying agent, and was dispensed and packaged, so as to obtain a finished product.

The invention claimed is:

1. An eye patch for alleviating eye fatigue and discomfort consisting essentially of therapeutically effective amounts of a mung bean germ extract, an eucalyptus leaf extract, a clove leaf extract, a mint leaf extract, a camphor leaf extract, and borneol.

2. The eye patch of claim 1, wherein the eye patch is prepared by a method consisting essentially of:
preparing the mung bean germ extract by cutting fresh mung bean germs coarsely and then mixing them with water of 0.3 to 0.5 times by weight; placing the mixed solution into an ultrasonic cell crusher to crush into a cell slurry; performing a centrifugation treatment on the cell slurry through a centrifuge to produce a supernatant; taking out the supernatant and then separating the supernatant through a sound membrane separator, thereby obtaining the mung bean germ extract having a molecular weight of less than 6000 daltons;
preparing the eucalyptus leaf extract by breaking mechanically fresh eucalyptus leaves and then adding water of 0.5 to 0.6 times by weight and mixing; placing the mixed solution into an ultrasonic cell crusher to crush into a cell slurry; performing a centrifugation treatment on the cell slurry through a centrifuge to produce a supernatant;

taking out the supernatant and then separating the supernatant through a sound membrane separator, thereby obtaining the eucalyptus leaf extract having a molecular weight of less than 6000 daltons;

preparing the mint leaf extract by mechanically breaking fresh mint leaves, and then adding water of 0.5 to 0.6 times by weight and mixing; placing the mixed solution into an ultrasonic cell crusher to crush into a cell slurry; performing a centrifugation treatment on the cell slurry through a centrifuge to produce a supernatant; taking out the supernatant and separating the supernatant through a sound membrane separator, thereby obtaining the mint leaf extract having a molecular weight of less than 6000 daltons;

preparing the clove leaf extract by mechanically breaking fresh clove leaves, and then adding water of 0.5 to 0.6 times by weight and mixing; placing the mixed solution into an ultrasonic cell crusher to crush into a cell slurry; performing a centrifugation treatment on the cell slurry through a centrifuge to produce a supernatant; taking out the supernatant and separating the supernatant through a sound membrane separator, thereby obtaining the clove leaf extract having a molecular weight of less than 6000 daltons;

preparing the extract of camphor leaves by mechanically breaking fresh camphor leaves, and then adding water of 0.5 to 0.6 times by weight and mixing; placing the mixed solution into an ultrasonic cell crusher to crush into a cell slurry; performing a centrifugation treatment on the cell slurry through a centrifuge to produce a supernatant;

taking out the supernatant and separating the supernatant through a sound membrane separator, so as to obtain the camphor leaf extract having a molecular weight of less than 6000 daltons;

mixing the above extracts and formulating them according to the parts by weight as defined above, and then performing a frozen centrifugation on them at a centrifugal rotation speed of 3000 rpm~4000 rpm for 10 to 20 minutes at a temperature in a range of 0~4° C. to remove sediments to form a centrifugation solution; separating the centrifugation solution again through a sound membrane separator, so as to obtain a mixture of extracts having a molecular weight of less than 6000 daltons; and mixing the mixture of extracts with borneol obtained after the mixing and separation to produce the eye patch.

* * * * *